(12) United States Patent
Schenk et al.

(10) Patent No.: US 8,633,809 B2
(45) Date of Patent: Jan. 21, 2014

(54) ELECTRODE DIVERSITY FOR BODY-COUPLED COMMUNICATION SYSTEMS

(75) Inventors: Tim Corneel Wilhelmus Schenk, Eindhoven (NL); Johannes Aldegonda Theodorus Marie van den Homberg, Weert (NL); Alberto Fazzi, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 731 days.

(21) Appl. No.: 12/809,123

(22) PCT Filed: Dec. 18, 2008

(86) PCT No.: PCT/IB2008/055413
§ 371 (c)(1),
(2), (4) Date: Jun. 18, 2010

(87) PCT Pub. No.: WO2009/081343
PCT Pub. Date: Jul. 2, 2009

(65) Prior Publication Data
US 2010/0315206 A1 Dec. 16, 2010

(30) Foreign Application Priority Data
Dec. 20, 2007 (EP) .................................... 07123774

(51) Int. Cl.
| | |
|---|---|
| *G09F 25/00* | (2006.01) |
| *G08B 23/00* | (2006.01) |
| *G08B 19/00* | (2006.01) |
| *G08B 1/00* | (2006.01) |
| *G08B 13/08* | (2006.01) |
| *G08B 13/14* | (2006.01) |
| *G08B 17/12* | (2006.01) |
| *G05B 23/02* | (2006.01) |

(52) U.S. Cl.
USPC ...... 340/286.01; 340/517; 340/522; 340/531; 340/545.4; 340/572.4; 340/573.1; 340/3.1; 600/547

(58) Field of Classification Search
USPC ..................................................... 340/286.01
See application file for complete search history.

(56) References Cited

U.S. PATENT DOCUMENTS

| | | | | |
|---|---|---|---|---|
| 4,121,576 A | * | 10/1978 | Greensite ...................... | 600/512 |
| 5,740,811 A | * | 4/1998 | Hedberg et al. ............... | 600/510 |
| 5,914,701 A | | 6/1999 | Gersheneld et al. | |
| 6,186,955 B1 | * | 2/2001 | Baura ........................... | 600/526 |
| 6,223,018 B1 | | 4/2001 | Fukumoto et al. | |
| 6,777,992 B2 | | 8/2004 | Ziesler et al. | |

(Continued)

FOREIGN PATENT DOCUMENTS

| | | |
|---|---|---|
| EP | 1798875 A1 | 6/2007 |
| JP | 2003143086 A | 5/2003 |

(Continued)

OTHER PUBLICATIONS

Thomas Guthrie Zimmerman, "Personal Area Networks (PAN): Near-Field Intra-Body Communication", Master of Thesis, Massachusetts Institute of Technology, Sep. 1995, pp. 1-81.

(Continued)

*Primary Examiner* — Jennifer Mehmood
*Assistant Examiner* — John Mortell

(57) ABSTRACT

The present invention relates to coupler device, processing apparatus and method of processing a plurality of body-coupled communication signals which have been detected by using an electrode arrangement with a plurality of electrodes or electrode segments (40, 42; 40, 43). Respective transmission parameters of the body-coupled communication signals are estimated and at least one of a selecting and weighting processing is applied to the detected body-coupled communication signals based on the estimated transmission parameters. Then, the processed body-coupled communication signals are combined to generate a diversity output signal. Thereby, robustness against coupler misplacement and user convenience is increased in body-coupled or body-based communication systems.

22 Claims, 6 Drawing Sheets

(56) References Cited

U.S. PATENT DOCUMENTS

| | | | |
|---|---|---|---|
| 6,882,940 B2 * | 4/2005 | Potts et al. | 702/23 |
| 6,992,565 B1 | 1/2006 | Giesler | |
| 7,783,345 B2 * | 8/2010 | Skrabal et al. | 600/547 |
| 2005/0192488 A1 * | 9/2005 | Bryenton et al. | 600/301 |
| 2006/0173265 A1 | 8/2006 | Kim et al. | |
| 2010/0036211 A1 * | 2/2010 | La Rue et al. | 600/301 |

FOREIGN PATENT DOCUMENTS

| | | | |
|---|---|---|---|
| JP | 2003188833 A | 7/2003 | |
| WO | 0178594 A1 | 10/2001 | |
| WO | 2006132058 A1 | 12/2006 | |
| WO | 2007049845 A2 | 5/2007 | |
| WO | 2007148877 A1 | 12/2007 | |

OTHER PUBLICATIONS

Katsuyuki Fujii et al, "Study on the Transmission Mechanism for Wearable Device Using the Human body as a transmission Channel", IEICE Trans. Commun. vol. E88-B, No. 6, Jun. 2005, pp. 2401-2410.

* cited by examiner

ELECTRODE DIVERSITY FOR BODY-COUPLED COMMUNICATION SYSTEMS

FIELD OF THE INVENTION

The present invention relates to a coupler device, processing apparatus and method of processing a plurality of body-coupled communication signals.

BACKGROUND OF THE INVENTION

Body coupled communications (BCC) or body-based communication has been proposed as a promising alternative to radio frequency (RF) communication as a basis for body area networks. BCC allows exchange of information between a plurality of devices which are at or in close proximity of a body of a human or an animal. This can be achieved by capacitive or galvanic coupling of low-energy electrical fields onto the body surface. Hence, the human body is exploited as a communication channel, so that communication can take place with much lower power consumption than in standard radio systems commonly used for body area networks (BANs, e.g. ZigBee or Bluetooth systems). Since BCC is usually applied in close proximity to the body, it can be used to realize new and intuitive body-device interfaces based on contact or proximity.

BCC can be technically realized by electric fields that are generated by a small body-worn tag, e.g., being integrated into a credit card or another suitable device attached to or worn in close proximity to the body. This tag capacitively or galavanicly couples a low-power signal to the body. Sometimes this body-coupled communication is referred to as "near-field intra-body communication". BCC is a wireless technology that allows electronic devices on and near the human body to exchange digital information through capacitive or galvanic coupling. Information is transmitted by modulating electric fields and either capacitively or galvanicly coupling tiny currents in the range of pico amperes onto the body. The body conducts the tiny current (e.g., 50 pA) to body mounted receivers. The environment (the air and/or earth ground) provides a return path for the transmitted signal.

FIGS. 1A and 1B show a general transmitter-receiver model of capacitive BCC, as described in Thomas Guthrie Zimmerman, *Personal Area Networks (PAN): Near-Field Intra-Body Communication*. Master of Thesis, Massachusetts Institute of Technology, September 1995. Both TX and RX elements are electronic battery powered devices, electrically isolated and having a pair of electrodes A and B, acting as reference and signal electrode. The transmitter and receiver electrodes A, B can be modelled as capacitor plates. Such capacitive BCC can be used for data exchange between devices in so-called personal area networks (PANs) or body area networks (BANs). A PAN prototype working at 330 kHz was developed to demonstrate the digital exchange of data through the body. Examples of such communication systems are disclosed for example in U.S. Pat. No. 6,992,565, U.S. Pat. No. 6,777,992, U.S. Pat. No. 6,223,018, and U.S. Pat. No. 5,914,701.

The electrodes A, B can be made of common printed circuit board (PCB) material with copper surfaces. The size could be approximately 3 cm×5 cm×1 cm. Measurements have shown reliable communication over the whole human body, regardless of the location of both TX and RX devices.

Although the devices FIGS. 1A and 1B have good sensitivity and give a strong signal even when the TX and RX devices are far apart on the body, the orientation of the RX/TX devices with respect to the human body is critical and largely influences the communication performance. For capacitive BCC, ideally, the TX and RX devices are lying flat on the body surface, with one electrode in close contact to the body and the other having "free sight" to the surroundings.

This is the case since the performance of capacitive BCC is influenced by a capacitive coupling between the transmitter (TX) and receiver (RX) devices and the human body and all surrounding conductors. In this scenario the most critical aspect is represented by the orientation of the devices with respect to the body. The signal attenuation strongly depends on the ratio between the capacitive coupling to human body of the signal electrodes and reference electrodes. The closer the coupling values the weaker the received/transmitted signal. A solution to this problem is crucial in order to have reliable communication between BCC devices that are not fixed to the human body but that can be also loosely placed around it, as in most of the possible scenarios.

In FIG. 1A both TX and RX devices are in a flat angle with respect to the human body. Electrodes B have thus a much stronger capacitance $C_{2b}$ to the body than to the surroundings (capacitance $C_{1b}$), while electrodes A are better coupled to the surroundings (capacitance $C_{1a}$) and have only small coupling to the body (capacitance $C_{2a}$). This way a signal that is applied between the TX electrodes will generate a voltage difference between the electrodes in the receiver, thereby enabling data transfer.

However, in FIG. 1B, the RX device is rotated by 90 degrees, which means that both electrodes A and B of the RX device have equal coupling to the body (capacitance $C_{2a}=C_{2b}$) and surroundings (capacitance $C_{1a}=C_{1b}$). As a result, any signal that is conducted by the body (as for instance a signal generated by the TX device) is common mode for electrodes A and B in the RX device. In other words, both electrodes A and B see the same potential and there is no voltage difference. The same holds for situations where the TX device is rotated by 90 degrees. In that case no signal is provided to the body and signal transfer is impossible. Of course, the 90 degree angle is a limit situation, but it will be clear that any other rotation (with respect to the ideal flat angle) will lead to a decrease of the received signal power.

In order to provide close contact and flat angle to the human body, it has been proposed to fix electrodes to the body (e.g. by means of stickers or elastic bands) but this puts a strong limit on the possible applications, since in most scenarios the TX/RX devices are expected to be only in proximity to the body and loosely coupled to it (e.g. any device that could placed in pocket, such as a mobile phone, or be integrated in textile). Moreover also in the case of devices that can be stitched to the human body (for example, medical sensors), movements of the user during normal life can affect the capacitance configuration of the transmitting/receiving devices in a way that reliable communication cannot be guaranteed.

Communications using BCC is thus sensitive to the orientation of the couplers relative to the body. Due to this sensitivity to the orientation of the couplers, the user is required to place and keep the BCC devices in a well-defined orientation. This creates user-inconvenience and unreliable transmission. Hence, it is desirable to make the BCC communication between devices which can be placed somewhere at the body reliable, so that the communication range for these devices is the whole body.

SUMMARY OF THE INVENTION

An object of the present invention is to increase robustness and user convenience in body-coupled or body-based communication systems.

This object is achieved by a coupler device as claimed in claim 1, an apparatus as claimed in claim 5, and a method as claimed in claim 16.

Accordingly, an adaptive configuration system is provided, so that, within a group of electrodes, the most suited electrodes for acting as signal electrodes (e.g. the ones with better than average coupling to the human body) and the most suited electrodes to act as reference electrodes (e.g. the ones with a lower than average coupling to the human body) can be selected. In this way, it is possible to substantially improve conditions under which the communication system operates, regardless of the position or orientation of transmission/reception devices with respect to the human body. The orientation sensitivity of the body-coupled communication can thus be reduced and robustness and user convenience can be increased. Multiple or segmented electrodes with mutual orientation difference are provided on or close to the body. This electrode diversity can then be applied to either select an electrode for a certain transmission or to combine signals from different couplers. In a specific embodiment the signals from the different couplers can be combined using a weighting sum.

Hence, a concept of electrode diversity, techniques to combine or select signals from the different electrodes, different methods to determine selection or combining parameters and a signaling method to allow for joint transmission and reception coupler diversity can be provided.

The electrodes could be configured in any number, in any shape, or can be arranged in any geometry. Thereby, the system is capable of selecting a desirable set of electrodes to be used as signal electrodes or as reference electrodes. Similarly, the combining parameters can be determined to combine the signals from the different electrodes. In these ways an electrode configuration with enhanced reception power or quality can thus be obtained for a given position and orientation with respect to the body, so that optimized and reliable communication can be achieved.

The electrode configuration can be statically (only at start-up) or dynamically (continuously or periodically) selected according to the application scenario. The selection of the configuration can be based e.g. on a capacitance estimation and can be controlled by hardware or software. The system and communication is then much less influenced by position, orientation or movements with respect to the human or animal body.

Additionally, the number of electrodes used as a reference or as signal couplers may be optimized. For example, if a small number of electrodes are enough to enable a correct coupling of the signal to the body, all the other electrodes can be selected as reference electrodes. This provides further optimization since capacitive coupling of the reference electrode(s) to surrounding conductors (earth ground) is one of the parameters that determine signal strength. The more capacitive coupling the stronger the signal.

The plurality of electrodes or electrode segments of the electrode arrangements may be arranged to provide during said body-coupled communication at least one of a horizontal orientation between signal and reference electrodes or electrode segments with respect to the surface of the human or animal body, a vertical orientation between signal and reference electrodes or electrode segments with respect to the surface of the human or animal body, and a signal-only orientation in which said electrode arrangement only cosists of signal electrodes, and wherein said plurality of electrodes or electrode segments differ by at least one of orientation and location to an extent sufficient to achieve said coupler diversity. Thereby, a high variety of orientations of individual electrodes or electrode segments can be provided, so that receipt of at least one strong signal is highly probable.

In a specific example, the plurality of electrodes or electrode segments may be arranged in a three-dimensional arrangement, which may further increase the diversity gain.

Furthermore, the plurality of electrodes or electrode segments may comprise first electrodes with a first conducting area and second electrodes with a second conducting area, said first conducting area having a bigger size than said conducting area. With this arrangement the electrode with the smaller conducting area can be used as a capacitor measurement electrode.

According to a first option, the estimation can be performed locally by determining at least one of a capacitance or a resistance between coupler electrodes through which the body-coupled communication signals have been received.

According to a second option, the estimation can be performed based on a training sequence received via a body-coupled communication signal. In a specific example, the estimation can be adapted to receive the training sequence in a preamble of a packet of the body-coupled communication signal.

According to a third option, the estimation can be performed based on a received data signal of the body-coupled communication signal. More specifically, the estimator may be adapted to estimate the transmission parameters, selection parameters or weighting parameters based on an error check of the received data signal.

The transmission parameters may be successively adapted for each of the plurality of body-coupled communication signals by using the selecting processing.

Moreover, a look-up table may be provided for storing estimated transmission parameters of body-coupled devices from which the plurality of body-coupled communication signals have been received.

Additionally, the estimated transmission parameters may be signaled back to body-coupled devices from which the plurality of body-coupled communication signals have been received.

The signal processing unit of the above apparatus may comprise a plurality of multipliers for selectively weighting the plurality of received body-coupled communication signals, and an adder for adding the weighted body-coupled communication signals.

As an alternative, the signal processing unit may comprise a plurality of comparators for comparing the strength of each of the plurality of body-coupled communication signals with an average strength or other threshold level, and a plurality of switches for selecting those body-coupled communication signals whose signal strength is higher than the average strength or other threshold to be combined to generate the output signal.

Further advantageous embodiments are defined below.

BRIEF DESCRIPTION OF THE DRAWINGS

The invention will now be described, by way of example, based on embodiments with reference to the accompanying drawings, wherein.

DESCRIPTION OF PREFERRED EMBODIMENTS

Various embodiments of the present invention will now be described based on a BCC system as an alternative to radio frequency (RF) communication for PANs and BANs. As already mentioned above, BCC signals are conveyed over the body instead of through the air. As such, the communication is confined to an area close to body, in contrast to RF communications, where a much larger area is covered. Therefore, TX and RX devices are situated on, connected to, or placed close to the body. This creates possibilities for many applications in the field of identification and security. Moreover, since lower frequencies can be applied than in RF communications, it opens the door to low-cost and low-power implementations of BAN/PAN. Data signals are not transmitted by antennas but using "couplers", consisting of e.g. electrodes. These couplers are configured to couple, e.g. galvanic or capacitive, the data signals to the body.

Figure 2A:
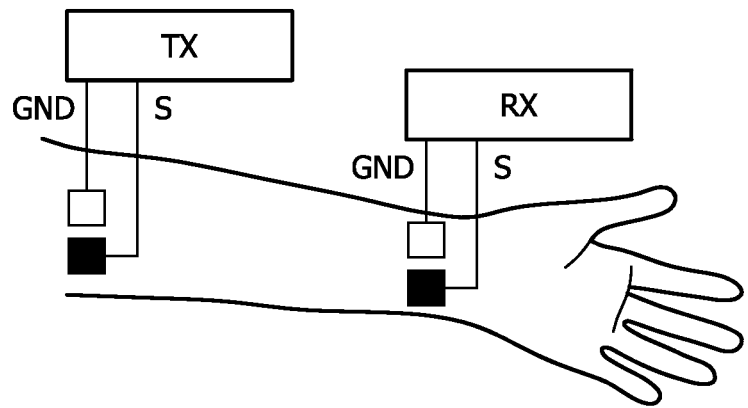
FIGS. 2A to 2C show electrode coupling setups with different reference and signal electrode orientations.
Figure 2B:
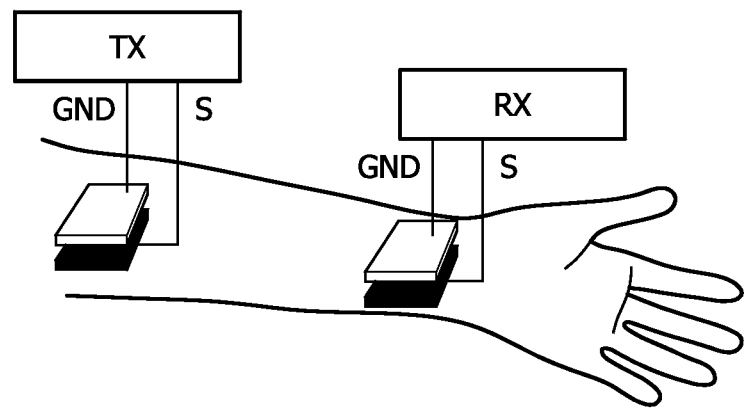
Figure 2C:
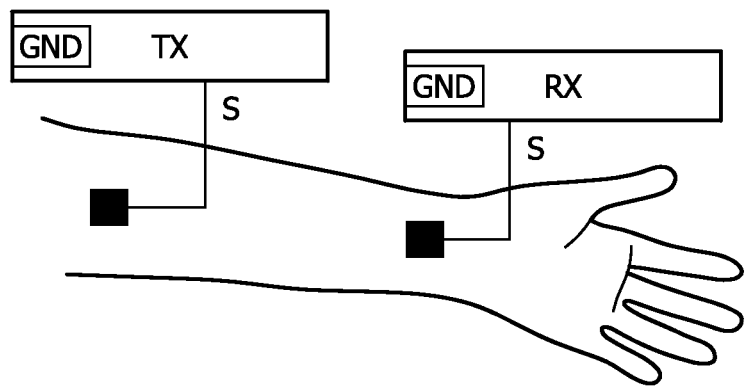

FIGS. 2A to 2C show possible electrode configurations for a BCC communication between a TX device and an RX device. More specifically, a communication setup over an arm is illustrated, where information is transmitted from the TX device to the RX device.

FIG. 2A shows a first coupling setup, where both signal level (S) and reference or ground level (GND) are placed close to or on the body and in this way both couple to the body. The corresponding electrodes of the couplers are configured to obtain a horizontal field orientation and is most often used for galvanic coupling. FIG. 2B shows a second coupling setup, where either the signal level (S) or the reference or ground level (GND) is coupled to the body, while the respective other level is coupled to the "air", "surroundings" or "earth ground". This second coupling setup provides a vertical field orientation and is most often used for capacitive coupling. The structure connected to the body consists of two isolated coupling electrodes, where one has to be directed towards the body and the other one is stacked parallel to it. FIG. 2C shows a third coupling setup where only one coupler is connected to or place close to the body, but where a ground plate (GND) of a PCB of the RX/TX devices may act as reference or ground electrode. The latter configuration is most often used for capacitive BCC.

Figure 1A:
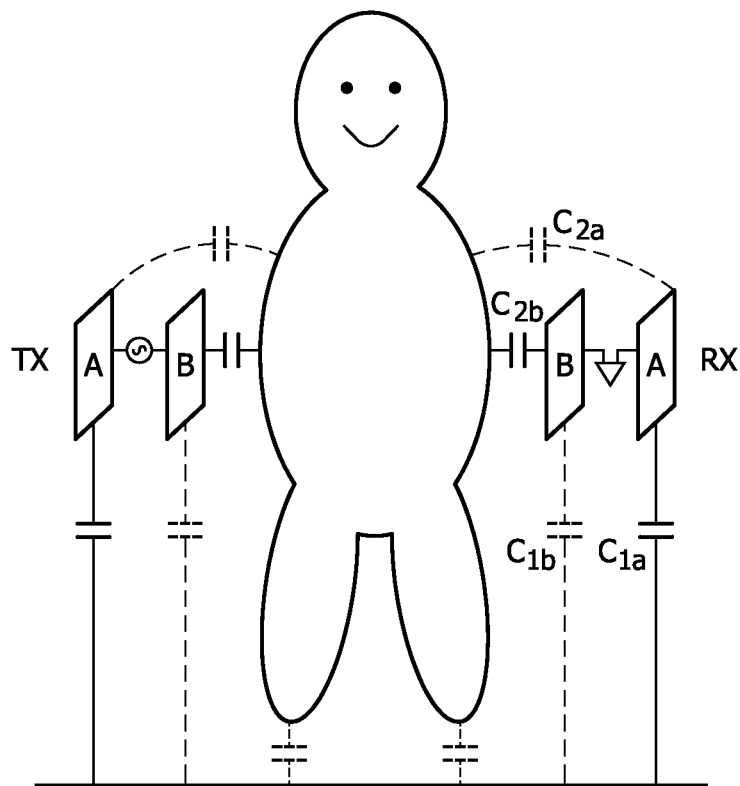
FIGS. 1A and 1B show schematic human bodies and the influence of device orientation on the coupling capacitors.
Figure 1B:
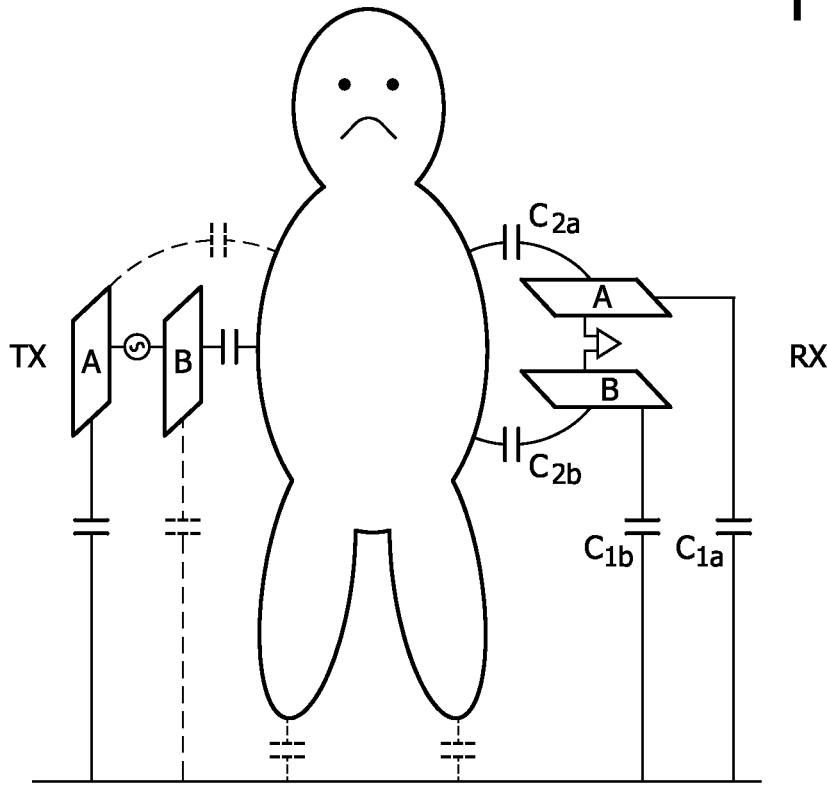

Instead of using only two electrodes (e.g. one that couples the signal to the body and one that is used as a reference) for the communication system, shown in FIGS. 1A and 1B as a pair of plates or electrodes A and B, a set of plates or electrodes (which can be in any number or shape) is provided in various embodiments. The set of electrodes is connected to an active configuration apparatus or system which selects which electrodes are coupled to the human body in order to use at least some of them as signal electrodes (e.g. in parallel), while at least some of the remaining electrodes are then used as reference electrode (e.g. also in parallel).

According to the embodiments described below, it is suggested to improve reliability, robustness and ease of use of BCC systems by applying electrode diversity with at least one of different orientations of the electrodes, different techniques to either combine the signals at the different electrodes or group and/or select (a subset of) them to create electrode diversity, and different procedures to determine a desired diversity setting, i.e., criteria or parameter(s) based on which diversity setting (e.g. selection of a coupler) can be controlled. As an additional option, a specific signaling could be applied from a receiver (RX device) to a transmitter (TX device) to allow the transmitter to apply or control its diversity setting based on measurements or determinations at the receiver.

The coupling configurations presented in FIGS. 2A to 2C are disadvantageous in that their performance is sensitive to the orientation of the coupler. In K. Fujii, et al., "Study on the Transmission Mechanism for Wearable Device Using the Human Body as a Transmission Channel," IEICE Trans Commun E88-B, pp. 2401-2410, it is indicated that the orientation shown in FIG. 2A has a 20 dB higher loss than when the electrodes are rotated by 90 degrees. Similar things are indicated for the coupling configurations shown in FIGS. 2B and 2C. For FIG. 2B it is indicated that when the couplers, i.e. pair of electrodes, are tilted, compared to the body, the received signal level largely degrades, as was explained in the above discussion of FIG. 1.B. It has also been shown that the performance is best when the GND reference electrode faces the ground.

According to embodiments of the present invention, orientation sensitivity is decreased by subdividing the electrode into smaller, separate electrodes or, similarly, providing additional electrodes compared to the setups presented in FIGS. 2A to 2C. The signals on the different electrodes are then combined and/or selected in such a way that for a given orientation of the body or electrode configuration maximum performance is achieved.

Figure 3:
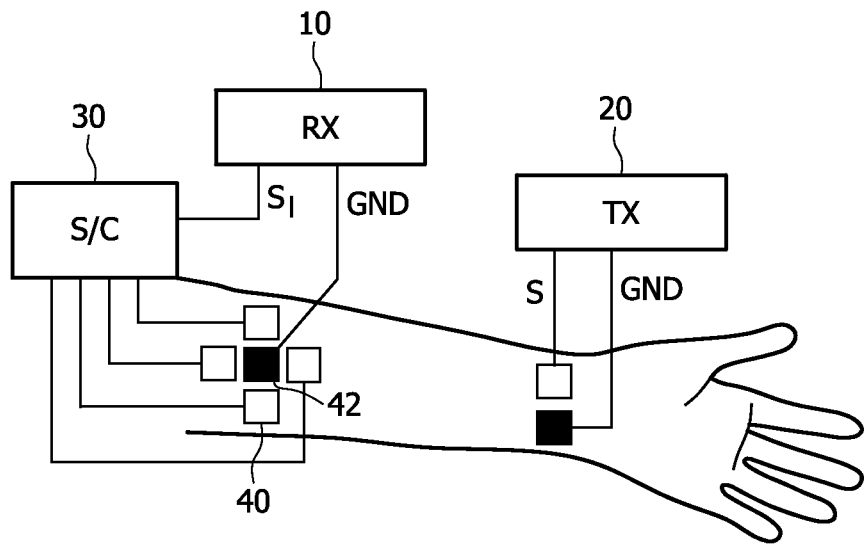
FIG. 3 shows an electrode arrangement with electrode diversity according to an embodiment.

FIG. 3 illustrates a possible diversity setup for the horizontal orientation of FIG. 2A. In this setup a receiver (RX) 10 comprises three additional signal electrodes 40 (e.g. plates or the like) compared to the original setup, wherein the signal electrodes 40 and a reference electrode 42 (colored in black and providing the GND signal) are connected to a selecting and/or combining unit 30 (which may be a hardware circuit or element or a software routine and which may be arranged as a separate unit or as a part of the receiver 10). Based on some acquired measures of performance or parameters, described later, the receiver 10 decides which electrode(s) 40 to use for reception of a data signal (i.e. selection) and/or how to combine the signals originating from a transmitter (TX) 20 and received by the different electrodes 40 (i.e. combination), and controls the selecting and/or combining unit 30 based on its decision. It is noted that for the purpose of illustration in FIG. 3, the reference electrode 42 is chosen to be fixed. However, in the selection diversity case, a pair of electrodes could be selected as well. Then, the present exemplary case of five electrodes 40 yields ten possible combinations instead of four with the fixed GND reference electrode 42. Alternatively, also different grouping of a set of electrodes as reference and another set of electrodes as signal electrodes could be achieved using this setup.

Moreover, the transmitter 20 not necessarily has to be a fixed electrode arrangement in FIG. 2. Rather, it could also be equipped with a similar diversity setup as the receiver 10. In this case, a pair of transmitter electrodes could be selected before transmission of the data signal, based on some performance or parameter measurement. In some coupler configuration it might be beneficial to do a joint optimization of the settings of the transmitter 20 and the receiver 10.

For the other coupler configurations of FIGS. 2B and 2C, different diversity setups can be made, which have similar properties to the setup in FIG. 3. For the vertical orientation of FIG. 2B, both signal and GND electrodes 40, 42 can be split in multiple separate electrodes which are separately connected to the selecting and/or combining unit 30. Moreover, such electrodes could be placed on a different angle, which reduces the impact of a certain orientation of the total device. An example could be a segmented bracelet, consisting of different electrode pairs. In such a configuration always at least one GND electrode is facing the surroundings or the ground and could be selected.

In the following, for clarity, the coupler setup of FIG. 3 will be considered for illustration purposes, although the measures and features are also applicable to the other scenarios.

Figure 4:
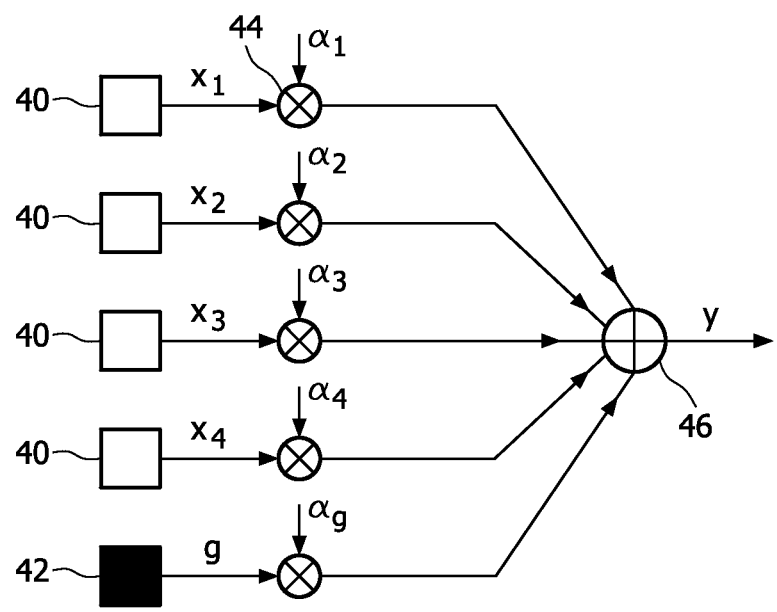
FIG. 4 shows a functional implementation of a diversity combiner according to an embodiment.

FIG. 4 shows a schematic functional diagram of a possible implementation of the selecting and/or combining unit 30. A received signal y obtained at the output of the combining and/or selecting unit 30, can be expressed as:

$$y = \sum_i \alpha_i x_i + \alpha_g g \quad (1)$$

where $x_i$ and $\alpha_i$ respectively denote the voltage of and weighting value for the ith electrode. The variable g denotes the GND reference voltage and the corresponding weight $\alpha_g$ would have an opposite sign to that for the other electrodes. For the selection combining approach $\alpha_i$ equals 1 for the selected signal electrode $i_{select}$ and 0 for all others signal electrodes and consequently $\alpha_g=-1$. Note that also a subset can be selected by setting $\alpha_i=1$ for a $i_{select,2}, \ldots$} and $\alpha_g=-1$. The signals $x_i$ and g are weighted by the respective multipliers 44 and then summed up by an adder 46 to obtain the output y.

In FIG. 3, four signal electrodes 40 and one GND electrode or reference couples 42 are provided. It is noted that for selection combining at least some of the multipliers 44 can be substituted by switches. For cases where also the reference electrode 42 is selected, the expression for the received signal becomes:

$$y = \sum_i \alpha_i x_i, \quad (2)$$

where $\alpha_i$ equals "1" for the selected signal electrodes and $\alpha_i$ equals "−1" for the selected reference electrodes and "0" for all others.

A procedure to determine i for the selection is based on maximizing the received voltage, i.e., $$i_{select} = \arg\max_i(|x_i - g|) = \arg\max_i(|x_i|). \quad (3)$$

Similarly for cases where both the signal electrodes 40 and the reference electrode 42 can be selected from a set of electrodes, wherein the set index equals:

$$(i, j)_{select} = \arg\max_{i,j}\left(\left|\sum_i \alpha_i x_i - \sum_j \alpha_j x_j\right|\right) \text{ for } i \neq j. \quad (4)$$

Another approach could be to base the decision of selection on an interference level of the signals from the different signal electrodes 40, e.g. by estimating the received power during the time no messages are transmitted.

Of course, when it is the goal to minimize the communication range of the proposed solution, for privacy and security reasons, a electrode or electrode pair which results in a desired or target signal quality (e.g. signal-to-noise ratio (SNR)) could be selected, rather than just the one with the highest possible signal quality.

Furthermore, instead of selecting one (or two) of the signal electrodes 40, the signals from different plates could be selected, which provides the advantage that the whole area of the electrode setup is applied. In that case, the weights in equations (1) and (2) are the relative weights of the different voltage contributions. A simple to implement solution would be to add all the signals with equal weight, i.e., $\alpha_i=1$ for all i. A more optimum solution is $\alpha_i=1/SNR_i$, where $SNR_i$ denotes the instantaneous signal-to-noise ratio for ith electrode connection.

When complex signals (I and Q) are used for body-coupled transmission, the received signal on the ith electrode can be written as:

$$x_i=\beta_i\exp(-j\theta_i)t, \quad (5)$$

where j denotes the complex unit, t denotes the transmitted (complex) signal $\beta_i$ and $\theta_i$ denote the amplitude and phase of the channel between the TX electrode and the ith RX electrode, respectively. In this case, a good way to determine the weights is based on maximum-ratio combining, i.e., $\alpha_i=\beta_i \exp(j\theta_i)$. A less complex method is based on equal gain combining, which yields $\alpha_i=\exp(j\theta_i)$, i.e., the signals from the different electrodes 40, 42 are coherently added.

Different methods to combine and select the signals (voltages) from the different electrodes 40, 42 have been described above. In the following, possible approaches for estimating the weighting parameters $\alpha_i$ or other parameters are presented. These approaches comprise for example offline estimation, training-based estimation, and data-aided parameter estimation.

For offline estimation, parameters can be estimated locally in the transmitter and/or receiver to determine the set of weighting coefficients $\{\alpha_i\}$. No transmission of data or training signal(s) is required. Several methods of offline estimation are described later, where for the case of capacitive coupling to the body the effective capacitance between pairs of electrodes is determined experimentally. Alternatively, in cases where the electrodes are galvanically coupled to the body, the resistance between the electrodes can be determined.

For selection combining, $\alpha_{i,j}=1$ is set where the capacitance is lowest and the resistance is highest, similarly to equations (1) and (2). For other diversity schemes, a function $f(.)$ exists, which maps the capacitance and resistance values $C_{i,j}$ and $R_{i,j}$ to the weighting values $\alpha_{i,j}$, i.e., $$\alpha_{i,j}=f(C_{i,j},R_{i,j}) \quad (6)$$

An example could be $\alpha_{i,j}=C_{i,j}^{-n}$, or $\alpha_{i,j}=R_{i,j}^{n}$, where n=1 or 2.

The advantage of offline estimation is that it can be applied during the periods when the system is not transmitting or receiving data and, thus, processing power is available. Also, it can be applied even where the transmitter and receiver are not in communication range.

For training-based estimation, a known sequence or training sequency is transmitted to enable estimation of the weighting parameters. This could be a separate packet which is transmitted to assess the body channel, also referred to as a "sounding packet". However, the preamble part of a packet transmission could be used also.

Figure 5:
FIG. 5 shows a schematic data packet for a training-based estimation of weighting parameters.

FIG. 5 shows a schematic data packet for a training-based estimation of the weighting or selection parameters. A preamble 50 is included in a packet transmission with a data portion 52, anyway, to enable synchronization and, as such, does not impose a large additional overhead. The preamble 50 may often consist of repeated symbols and can be used in this embodiment to convey the training sequence. Typical parameters, which would be estimated in such a procedure, are $\beta_i$, $\theta_i$ and $SNR_i$.

Figure 6:
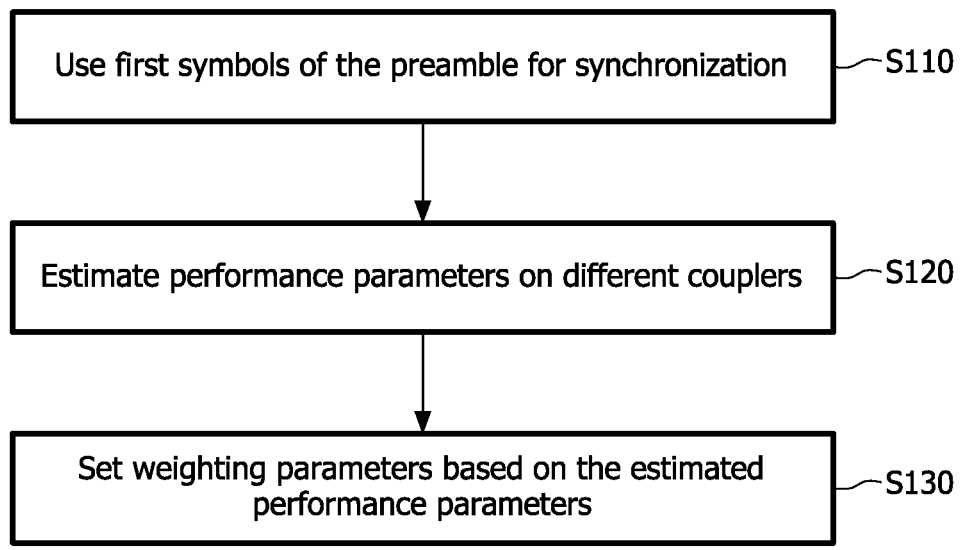
FIG. 6 shows a flow diagram of an estimation procedure according to an embodiment.

FIG. 6 shows a flow diagram of a procedure for estimating RX parameters, according to an embodiment.

In step S110, the receiver 10 uses the first symbols of the preamble 50 to get into synchronization. Subsequently, in step S120, performance parameters are measured on the different electrodes 40, e.g. one-by-one, to obtain estimated performance parameters. This can be enabled by setting $\alpha_i=1$ for only one i. At the symbol boundary the receiver 10 switches to the next electrode by setting $\alpha_{i+1}=1$ and $\alpha_i=0$. As such, the parameters corresponding to the different electrodes are successively estimated. In step S130, just before the data is received, the estimated parameters, e.g., $\beta_i$ and $\theta_i$ are used to set the weighting parameters $\alpha_i$ to the correct values for the reception of data.

It is noted that for many i values or a big number of (i,j), a large overhead is required (i.e. a long preamble) to estimate all parameters. This overhead can, however, considerably be reduced by storing the parameters of previous packets. Then, when the time constants of the channel are low compared to the packet repetition rate, only the parameters for a subset of the RX electrodes 40 have to be estimated per packet.

For data-aided parameter estimation, a received and/or detected data signal is used to estimate the parameters. Based on a detected symbol, the amplitude, $\beta_i$ and phase $\theta_i$ of the channel can be determined, e.g., based on the following equation:

$$\hat{\beta}_i \exp(-j\hat{\theta}_i) = \hat{t}^{-1} x_i,$$

where $\hat{t}$ is the estimate of the transmission signal derived from the detected data. Another approach could be to base the selected electrode(s) on a cyclic redundancy check (CRC) of the packet. When this check shows that the packet is detected incorrectly, the receiver 10 may switch to another electrode. An advantage of this method is that no extra overhead is required.

In this case of a coupler diversity at the transmitter side, two signaling methods can be applied alone or in combination, namely using the reciprocity of the body channel or using feedback of the channel parameters.

In the first signaling method, all BCC devices act as a transceiver, i.e., have both transmitter and receiver functionalities. Furthermore, reciprocity of the body channel is used, which means that the channel from a first device to a second device is equal to that from the second device to the first device. The transmitter can thus use the parameters, e.g., $\beta_i$, $\theta_i$ and $SNR_i$, estimated during a receiving phase (from the same device) to determine the values of the weighting parameters $\alpha_i$. These parameters can be based on either one of the above estimation methods.

For this first signaling method, the transceiver could be equipped with a look-up table storing the previous estimated parameters for all other devices. This number will, however, be low for BANs, since the number of nodes on a human or animal body will be limited.

In the second signaling method, the receiver estimates the channel parameters and after detection of the data part of the packet, it transmits these estimated values back to the sources (i.e. transmitter sides), which can apply them for the following transmission. Alternatively, the receiver can determine the $\alpha_i$ values for the transmitter and feed those back. In this way the receiver can optimize jointly for the TX and RX, which will lead to an improved performance. To enable this estimation process for different TX configurations, the transmitter can switch between coupler plates within the preamble period, e.g., every preamble symbol is transmitted by another electrode.

The proposed transmission system is thus capable of selecting a set of electrodes to be used as signal electrodes or as reference electrodes. The proposed system may consist of a set of electrodes that are supposed to be connected to a BCC device, a sensing circuit or functionality that, following different principles provides information about the capacitance between one single electrode and the rest of the world, a configuration controller or functionality that, based on the information provided by the sensing circuit or functionality, decides which electrodes should be considered as a coupler to the human body and which ones should be considered as transmitting electrodes (couplers to the external surroundings, e.g. earth ground). In the exemplary arrangement of FIG. 3, the sensing and configuration functionality may be provided by the selecting and/or combining unit 30.

Figure 7:
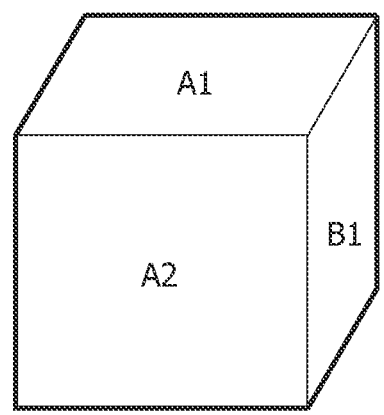
FIG. 7 shows an example of a multiple-electrode arrangement according to an embodiment.

FIG. 7 shows an example of a multiple-electrode arrangement according to an embodiment. In general, the electrodes can be of any shape, any size and can be arranged in any geometrical configuration. Nevertheless, geometries that provide a three-dimensional (3D) distribution of the electrodes, such as the arrangement of FIG. 7 provide a high probability of selecting two sets of electrodes with largely different aggregate capacitance to the human body, which is beneficial for capacitive based BCC.

A solution to find the optimal arrangement could be to simply try all (or a set of) different electrode arrangements and determine which one is best. As described above, this could be achieved via communication with another receiver or transmitter or by switching the device in a transmission mode and measure the current consumption in the output driving buffer. The electrode configuration that gives the lowest current consumption is the optimal one, as it makes sure that all electrodes with a large capacitance to the body are grouped together, providing good coupling to the body. All other electrodes apparently have a small capacitance to the body, which means that they must have "free sight" to the surroundings so that they can be grouped together as a combined transmitting surface. When the circumstances change, e.g. when the orientation of the device changes, an old configuration could be used, even when transmission is lost, until a new sweep through all different electrode arrangements is performed. Such a sweep could thus be performed regularly.

Figures 8A, 8B:
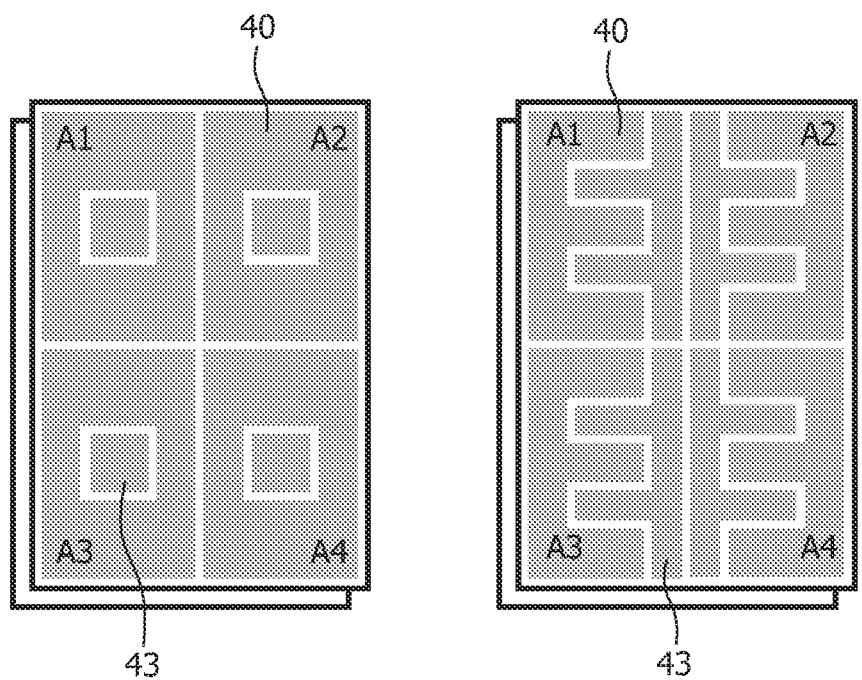
FIGS. 8A and 8B shows examples of splitted electrodes according to embodiments.

FIGS. 8A and 8B show examples of electrode arrangements according to other embodiments where each electrode A1 to A4 is split into two conductors, e.g., one big conductor to be used as a BCC electrode 40 for the BCC communication and one small conductor to be used as a measurement node 43 for capacitance measurement. The conductors can be of any shape and size.

With this arrangement, the capacitive coupling between the BCC electrode 40 and its corresponding sensing or measurement electrode 43 is strongly influenced by the presence of conductor surfaces in the environment. If an isolated conducting surface (as the human body) is close to the electrode, the capacitance between the BCC electrode 40 and the measurement electrode 43 increases. This difference can be easily sensed by applying a known signal to the BCC electrode 40 and evaluating the amplitude of the signal at the measurement electrode 43. This operation can be performed in parallel or serial for all electrodes belonging to the BCC signal. Moreover, the measurement could be performed during standard operation, by using a frequency band different with respect to the one used for signalling, or could be performed just before the beginning of a transmission or reception phase, or could be performed on a periodic base (determined by the desired application).

Once the capacitance measurement has been performed, it is easy to sort the electrodes into groups, e.g., those electrodes that show a higher capacitance to external conductors are the one that are selected as couplers to the human body, i.e. signal electrodes, and the other electrodes are those that are selected as reference electrodes.

With this topology it is also easy to adapt the number of electrodes that belong to the various groups. The mean capacitance value to the body can be estimated and for example each electrode that shows a capacitance larger than the mean value can be selected as electrode to the human body, while the other electrode(s) should be selected as electrodes to the environment. In this case, only the electrodes that give a major contribution to the capacitive coupling to the human body are selected as signal electrodes, even if their number is small.

Figure 9:
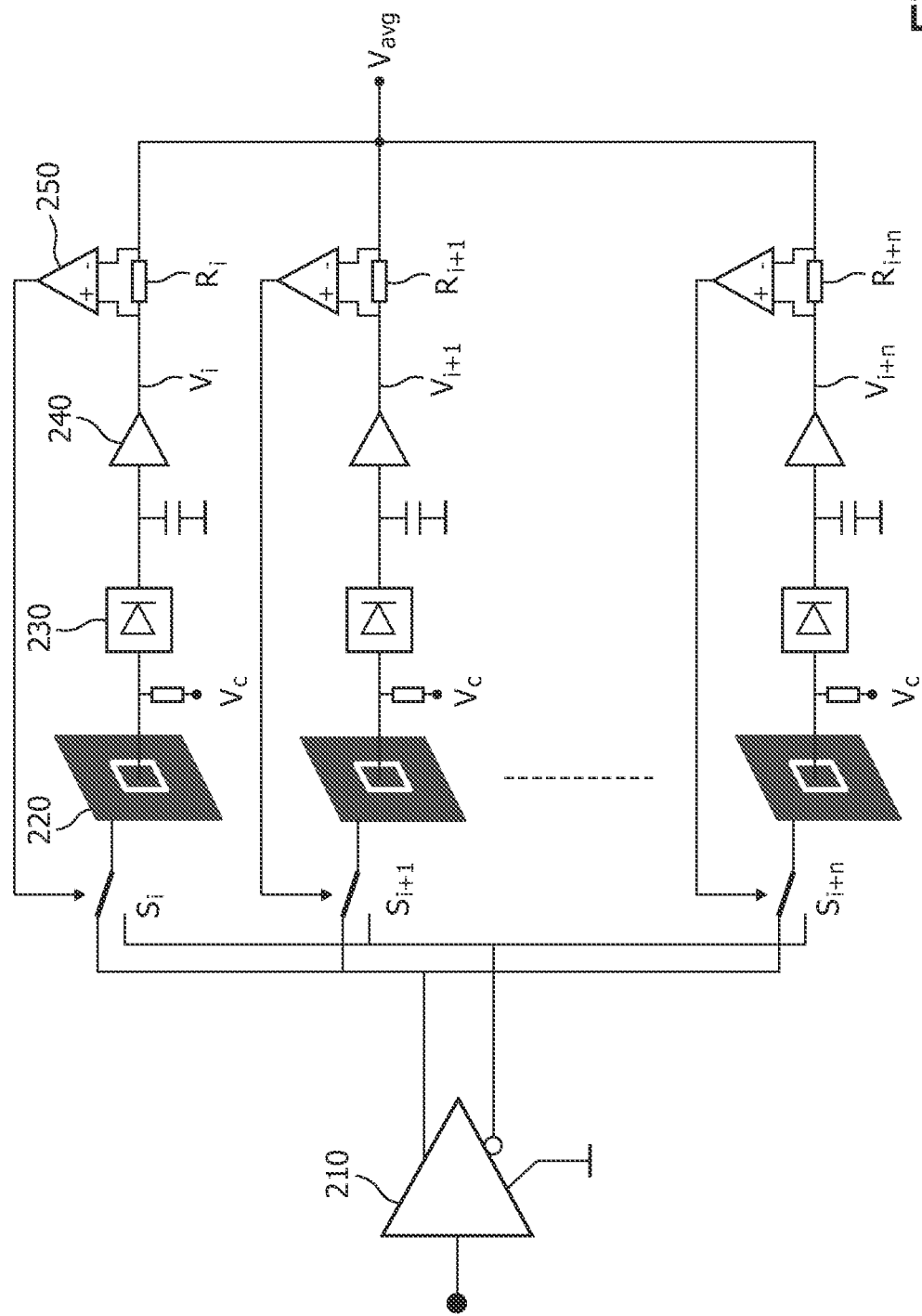
FIG. 9 shows a schematic diagram of a control circuit for controlling an electrode arrangement according to an embodiment.

FIG. 9 shows a schematic diagram of a control circuit topology for controlling an electrode arrangement according to an embodiment.

The capacitance between a BCC electrode and its corresponding measurement electrode is a measure for the distance between that electrode 220 and a conducting (e.g. human-) body. The capacitance can be measured by applying a known signal to the electrode and measuring the amplitude of the resulting signal at the measurement electrode with a predetermined load. This load is shown in FIG. 9 as a resistor to a common voltage $V_c$, but in principle any impedance, e.g. a capacitor, a coil or combination thereof can be used. Also, in the embodiment from FIG. 9 the known signal is derived directly from a modulated input transmission signal supplied to a buffer amplifier 210 with non-inverted and inverted outputs. This is possible due to the fact that the amplitude of the inverted transmission signal at the inverted output is equal to that of the original transmission signal, which means that the output of each amplitude detector 230 is independent of the position of a corresponding input switch $S_i$. Of course, it is also possible to use an extra, independent signal source, at an out-of-band frequency, to provide the known measurement signal. The output of each amplitude detector 230 is buffered at a buffer 240 to obtain a DC voltage $V_i$ which represents the signal strength and which is connected via equal resistors $R_i$ to $R_{i+n}$ to a summing node, giving the average voltage $V_{avg}$ of all individual $V_i$ voltages. Each branch has a comparator 250 which determines whether the individual voltage $V_i$ is higher or lower than the average voltage $V_{avg}$, and based on this decision the corresponding electrode is connected via switch $S_i$ to either the transmission signal or the inverted transmission signal. Thereby, all electrodes that show a higher than average capacitance (close to the body) will be grouped and connected to one phase of the transmission signal, while all others will be connected to the opposite phase of the transmission signal.

It is however noted that the configuration of FIG. 9 is only an example of how the system can be built. An equivalent setup could also be obtained with different building blocks or, after an analog-to-digital (A/D) conversion, in the digital domain and thus also on the basis of software routines.

During transmission the proposed configuration will be immediately and continuously altered when the conditions (e.g. orientation of the device) change. During a receiving mode, the last configuration of a prior transmission mode can be used, or an out-of-band signal can be applied to all electrodes, which should not affect the in-band received signals but allows continuous adaptation of the electrode arrangement.

The above embodiments can be implemented as adaptive body-coupled or body-based systems in many domains. In the field of consumer electronics, wireless connections can be set up more easily. As the number of available electronic devices increases (home computer, laptop, pocket pc, mobile phone . . . ) the interaction between these devices becomes more and more arduous to set up for common users. As facilitating tool BCC systems can help to connect several different devices using heterogeneous platforms and protocols. For example, with BCC a Bluetooth connection between a laptop and a mobile phone can be set-up by simple touch of the two devices allowing e.g. a photo exchange application.

BCC can also be used to realize applications which provide more convenience in the automotive area. Examples are car entry where a car can be opened by just touching it, theft protection, which allows only operating the car for specified users, wearing an identification tag, car configuration/personalization, which takes away the burden from the user to adjust the car settings to his/her personal preferences, the user is immediately recognized when entering the car.

Moreover, automatic identification is increasingly required in medical applications, both to improve patient safety, and workflow efficiency. Patient identifiers based on body-coupled communication allow for automatic recognition of patients during medical examinations, safe & automatic association of devices, sensors and wireless measurements to individual patients.

In all the above fields of application, the solution described in the above embodiments significantly increases reliability of the body channel communication.

In summary, a coupler device, processing apparatus and method of processing a plurality of body-coupled communication signals which have been detected by using an electrode arrangement with a plurality of electrodes or electrode segments have been described. Respective transmission parameters of the body-coupled communication signals are estimated and at least one of a selecting, grouping and weighting processing is applied to the detected body-coupled communication signals based on the estimated transmission parameters. Then, the processed body-coupled communication signals are combined to generate a diversity output signal.

While the invention has been illustrated and described in detail in the drawings and the foregoing description, such illustration and description are to be considered illustrative or exemplary and not restrictive. The invention is not limited to the disclosed embodiments. From reading the present disclosure, other modifications will be apparent to persons skilled in the art. Such modifications may involve other features which are already known in the art and which may be used instead of or in addition to features already described herein.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality of elements or steps. A single processor or other unit may fulfill the functions of the selecting and/or combining unit 30, e.g. as described in connection with FIGS. 4 and 6, based a corresponding software routines. The computer program may be stored/distributed on a suitable medium, such as an optical storage medium or a solid-state medium supplied together with or as part of other hardware, but may also be distributed in other forms, such as via the Internet or other wired or wireless telecommunication systems. The mere fact that certain measures are recited in mutually different dependent claims does not indicate that a combination of these measures cannot be used to advantage. Any reference signs in the claims should not be construed as limiting the scope thereof.

The invention claimed is:

1. A coupler device for a body-coupled communication, said coupler device being configured to be placed at or in close proximity to a human or animal body and comprising:
  an electrode arrangement consisting of a plurality of electrodes or electrode segments adapted to be separately connectable and having different mutual orientations with respect to the surface of said human or animal body to achieve electrode diversity,
  wherein a first subset of said plurality of electrodes comprise signal electrodes for receiving data signals, said signal electrodes having higher than average electrical coupling to the human or animal body and a second subset of said plurality of electrodes comprise reference electrodes having lower than average electrical coupling to the human or animal body, and
  wherein the average electrical coupling is a pre-determined threshold level based on an average detected signal strength of the plurality of electrodes;
  wherein signals from the different subsets of electrodes are combined to provide enhanced reception power or quality for the different mutual orientations of the electrodes or electrode segments of the electrode arrangement.

2. The coupler device according to claim 1, wherein said plurality of electrodes or electrode segments are arranged to provide during said body-coupled communication said different mutual orientation differences comprising:
  at least one of a horizontal orientation between signal and reference electrodes or electrode segments with respect to the surface of said human or animal body,
  a vertical orientation between signal and reference electrodes or electrode segments with respect to the surface of said human or animal body, and
  a signal-only orientation in which said electrode arrangement only consists of signal electrodes, and wherein said plurality of electrodes or electrode segments differ by at least one of orientation and location to an extent sufficient to achieve said electrode diversity.

3. The coupler device according to claim 1, wherein said plurality of electrodes or electrode segments are arranged in a three-dimensional arrangement.

4. The coupler device according to claim 1, wherein said plurality of electrodes or electrode segments comprise first electrodes with a first conducting area and second electrodes with a second conducting area, said first conducting area having a bigger size than said second conducting area.

5. An apparatus for processing a plurality of body-coupled communication signals, said apparatus comprising:
  a) a plurality of input terminals for receiving said plurality of body-coupled communication signals, wherein said plurality of input terminals are coupled to a respective plurality of electrodes or electrode segments adapted to be separately connectable and having different mutual orientations with respect to the surface of a human or animal body to achieve electrode diversity, wherein a first subset of said plurality of electrodes comprise signal electrodes for receiving said body-coupled communication signals, said first subset of signal electrodes having higher than average electrical coupling to the human or animal body and a second subset of said plurality of electrodes comprise reference electrodes having lower than average electrical coupling to the human or animal body, and wherein the average electrical coupling is a pre-determined threshold level based on an average detected signal strength of the plurality of electrodes;
  b) an estimator for estimating respective transmission parameters of said body-coupled communication signals; and
  c) a signal processor for applying at least one of a selecting and weighting processing to said received body-coupled communication signals and for combining the processed body-coupled communication signals to generate a diversity output signal, wherein said selecting and weighting processing is controlled based on said estimated transmission parameters.

6. The apparatus according to claim 5, wherein said estimator is adapted to estimate said transmission parameters locally by determining at least one of a capacitance or a resistance between coupler electrodes through which said body-coupled communication signals have been received.

7. The apparatus according to claim 5, wherein said estimator is adapted to estimate said transmission parameters based on a training sequence received via a body-coupled communication signal.

8. The apparatus according to claim 7, wherein said estimator is adapted to receive said training sequence in a preamble of a packet of said body-coupled communication signal.

9. The apparatus according to claim 5, wherein said estimator is adapted to estimate said transmission parameters based on a received data signal of said body-coupled communication signal.

10. The apparatus according to claim 9, wherein said estimator is adapted to estimate said transmission parameters based on an error check of said received data signal.

11. The apparatus according to claim 5, wherein said estimator is adapted to estimate said transmission parameters successively for each of said plurality of body-coupled communication signals by using said selecting processing.

12. The apparatus according to claim 5, wherein said apparatus comprises a look-up table for storing estimated transmission parameters of body-coupled devices from which said plurality of body-coupled communication signals have been received.

13. The apparatus according to claim 5, wherein said apparatus comprises a transmitter for transmitting the estimated transmission parameters back to body-coupled devices from which said plurality of body-coupled communication signals have been received.

14. The apparatus according to claim 5, wherein said signal processing unit comprises a plurality of multipliers for selectively weighting said plurality of received body-coupled communication signals, and an adder for adding the weighted body-coupled communication signals.

15. The apparatus according to claim 5, wherein said signal processing unit comprises a plurality of comparators for comparing the strength of each of said plurality of body-coupled communication signals with a predetermined threshold, and a plurality of switches (S) for selecting those body-coupled communication signals whose signal strength is higher than said predetermined threshold to be combined to generate said output signal.

16. A method of processing a plurality of body-coupled communication signals, said method comprising:
  a) detecting body-coupled communication signals by using an electrode arrangement with a plurality of electrodes or electrode segments having different mutual orientations with respect to the surface of said human or animal body to achieve electrode diversity, wherein a first subset of said plurality of electrodes or electrode segments comprise signal electrodes for receiving data signals, said signal electrodes having higher than average electrical coupling to the human or animal body and a second subset of said plurality of electrodes comprise reference electrodes having lower than average electrical coupling to the human or animal body, wherein the average electrical coupling is a pre-determined threshold level based on an average detected signal strength of the plurality of electrodes;
  b) estimating respective transmission parameters of said body-coupled communication signals; and
  c) processing the received body coupled communication signals by applying at least one of a selecting and weighting processing based on said estimated respective transmission parameters; and
  d) combining the processed body-coupled communication signals to generate a diversity output signal.

17. The method according to claim 16, further comprising performing said estimating locally by determining at least one of a capacitance or a resistance between respective ones of said coupler electrodes or electrode segments, through which said body-coupled communication signals have been received.

18. The method according to claim 16, further comprising estimating said transmission parameters based on a training sequence received via a body-coupled communication signal.

19. The method according to claim 16, further comprising estimating said transmission parameters based on a received data signal of said body-coupled communication signal.

20. The method according to claim 16, further comprising estimating said transmission parameters successively for each of said plurality of body-coupled communication signals by using said selecting processing.

21. The method according to claim 16, further comprising signaling the estimated transmission parameters back to body-coupled devices from which said plurality of body-coupled communication signals have been received.

22. A computer program product in one or more non-transitory computer-readable media, comprising code means that, when executed by a computer, causes the computer to perform actions of:
  a) detecting body-coupled communication signals by using an electrode arrangement with a plurality of electrodes or electrode segments wherein a first subset of said plurality of electrodes or electrode segments comprise signal electrodes for receiving data signals, said signal electrodes having higher than average electrical coupling to the human or animal body and a second subset of said plurality of electrodes comprise reference electrodes having lower than average electrical coupling to the human or animal body, wherein the average electrical coupling is a pre-determined threshold level based on an average detected signal strength of the plurality of electrodes;
  b) estimating respective transmission parameters of said body-coupled communication signals; and
  c) processing the detected body-coupled communication signals by applying at least one of a selecting and weighting processing to said body-coupled communication signals based on said estimated transmission parameters; and
  d) combining the processed body-coupled communication signals to generate a diversity output signal.

* * * * *